United States Patent
Wiesener et al.

(10) Patent No.: US 9,764,072 B2
(45) Date of Patent: Sep. 19, 2017

(54) METHOD FOR OPERATING A PUMP DEVICE AND A PUMP DEVICE

(71) Applicant: Berlin Heart GmbH, Berlin (DE)

(72) Inventors: Constantin Wiesener, Potsdam (DE); Dominik Karch, Berlin (DE)

(73) Assignee: Berlin Heart GmbH, Berlin (DE)

( * ) Notice: Subject to any disclaimer, the term of this patent is extended or adjusted under 35 U.S.C. 154(b) by 0 days.

(21) Appl. No.: 15/030,522

(22) PCT Filed: Oct. 21, 2014

(86) PCT No.: PCT/EP2014/072577
§ 371 (c)(1),
(2) Date: Apr. 19, 2016

(87) PCT Pub. No.: WO2015/059158
PCT Pub. Date: Apr. 30, 2015

(65) Prior Publication Data
US 2016/0263300 A1   Sep. 15, 2016

(30) Foreign Application Priority Data
Oct. 22, 2013   (EP) .................................. 13189738

(51) Int. Cl.
*A61M 1/10* (2006.01)
*A61M 1/12* (2006.01)
*A61M 1/00* (2006.01)

(52) U.S. Cl.
CPC ............ *A61M 1/1086* (2013.01); *A61M 1/10* (2013.01); *A61M 1/1029* (2014.02); *A61M 1/1096* (2014.02); *A61M 1/122* (2014.02); *A61M 1/0023* (2013.01); *A61M 2230/005* (2013.01); *A61M 2230/63* (2013.01)

(58) Field of Classification Search
None
See application file for complete search history.

(56) References Cited

U.S. PATENT DOCUMENTS

2005/0250975 A1* 11/2005 Carrier .................. A61M 1/101
                                                              600/16
2006/0052737 A1   3/2006  Bertrand et al.
2010/0268334 A1  10/2010  Pate et al.

FOREIGN PATENT DOCUMENTS

WO   WO 97/42414 A1   11/1997
WO   WO 2013/119752 A2   8/2013

* cited by examiner

*Primary Examiner* — Brian T Gedeon
(74) *Attorney, Agent, or Firm* — Brinks Gilson & Lione

(57) ABSTRACT

A method may be provided for the operation of a pump device, which comprises at least one pump as well as a suction element which is connected to the at least one pump and which has a suction opening positioned in a cavity of a body of a patient that sucks a fluid by way of producing a reduced pressure in the suction element, wherein an acceleration is measured and monitored during the operation of the pump device, wherein the reduced pressure in the suction element is reduced at least for a limited reaction time period, given the occurrence of an acceleration variable which lies above a fixed threshold valve. A correspondingly configured pump device may be provided.

12 Claims, 3 Drawing Sheets

METHOD FOR OPERATING A PUMP DEVICE AND A PUMP DEVICE

CROSS-REFERENCE TO RELATED APPLICATIONS

This application is a 371 nationalization of PCT/EP2014/072577, entitled "METHOD FOR OPERATING A PUMP DEVICE AND A PUMP DEVICE," having an international filing date of Oct. 21, 2014, the entire contents of which are hereby incorporated by reference, which in turn claims priority under 35 USC §119 to European patent application 13189738.1 filed on Oct. 22, 2013, entitled "Verfahren zum Betrieb einer Pumpeneinrichtung sowie Pumpeneinrichtung," the entire contents of which are hereby incorporated by reference.

TECHNICAL FIELD

The invention lies in the field of engineering, specifically of precision engineering and electrical technology, and can be particularly advantageously applied in the field of medical technology.

BRIEF DESCRIPTION OF THE DRAWINGS

The invention is hereinafter represented in a drawing by way of an embodiment example and subsequently explained. There are shown in.

DETAILED DESCRIPTION

Figure 1:
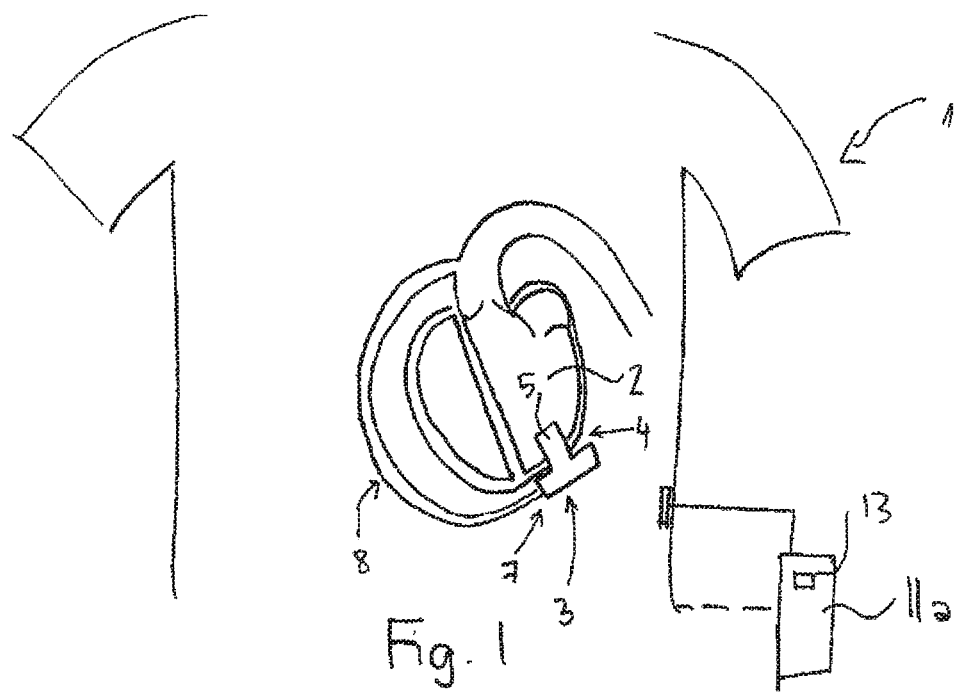
FIG. 1 schematically, the representation of a body of a patient with a heart catheter pump, which is introduced into a ventricle via the aorta, FIG. 2 in an enlarged representation, a heart catheter which is introduced through an aortic arch and is with a heart pump, FIG. 3 with regard to time, the measurement data of an acceleration sensor and the reaction in the form of the influencing of the suction pressure, FIG. 4 schematically, a control and data processing part of the pump device as well as FIG. 5 schematically, the representation of rotation pump.

Specifically, the invention for example can be applied to a pump device with a pump for sucking a fluid into a cavity of a body of a patient. Apart from this, applications outside the medical field, where fluids are to be sucked out a cavity by way of a pump device, are also conceivable.

It is particularly in the medical sector that high technical demands are placed on pumps for the delivery fluid in the body of a patient. In this context, blood pumps which suck blood at a first location in the blood vessel system of a patient and deliver this blood to a second location within or outside the blood vessel system are known for example.

For this purpose, a pump which on the one hand is arranged within the body of a patient, but on the other hand can also be arranged outside the body of a patient, is connected to a catheter which at least partly is located in the blood vessel system of the patient and comprises a suction opening there. Such a catheter for example can comprise a suction opening in a ventricle of a patient.

A known problem on sucking or suctioning blood lies in the fact that such a catheter can attach itself by suction to a vessel wall due to the prevailing reduced pressure, by which means the suction opening is closed and the further sucking of blood is made impossible. Furthermore, the vessel wall can thereby become permanently damaged.

It is known from the state of the art, for example to arrange pigtail ends for example in the region of the suction opening of a catheter, in order to establish a minimum distance between a suction opening and a vessel wall in a mechanical manner. However, on the one hand the contact with the vessel walls cannot be completely prevented by this measure, and on the other hand it is the tendency of such a pigtail to permanently hit the vessel walls, which likewise entails the danger of tissue irritation.

Against the background of the state of the art, it is therefore the object of the present invention to create a method for the operation of a pump device and a corresponding pump device, which avoids the outlined problems and permits a permanent and reliable suctioning of a fluid via a suction opening.

Accordingly, the invention relates to a method for operation of a pump device comprising at least one pump as well as a suction element which is connected to this pump, said suction element having a suction opening, said pump sucking a fluid by way of producing a reduced pressure in the suction element, in a cavity, in particular of a body of a patient, wherein an acceleration is measured and monitored during the operation of the pump device. The object is achieved by way of the reduced pressure in the suction element being reduced at least for a limited reaction time period, given the occurrence of an acceleration variable or a variable which is derived from this, which lies above a fixed threshold value.

The invention is based on the recognition that the suction attachment of a suction element with a suction opening on a vessel wall or generally on a wall of a cavity is often effected due to the fact that the vessel which forms the cavity, thus for example a body of a patient or other body with a cavity, is accelerated and parts of the pump device, in particular the suction element, inasmuch as it is not fixed with respect to the walls of the cavity, carry out a relative movement to the walls of the cavity due to this. Expressed differently, the parts of the pump device in the cavity move given an acceleration of the vessel comprising the cavity and thereby easily hit the walls of the cavity, by which means the danger of a suction attachment exists.

This danger can be considerably reduced by way of the reduced pressure in the suction element being at least temporarily reduced given the occurrence of certain acceleration conditions. The suction pressure can be increased again as soon as the movement has come to a rest or into a stable condition.

A control of a rotating blood pump in dependence on an acceleration variable is basically known from the state of the art. A system, with which the physical activity of a patient is monitored by acceleration sensors and the speed of the blood pump is controlled in dependence on acceleration variables is described in the US patent application US 2008/0183287. There, the control is directed towards the purpose of increasing the assistance of the heart by way of a blood pump, in the case of increased bodily activity of a patient, and therefore of usefully increasing the pump power with the occurrence of permanently high accelerations.

The present invention in contrast is not aimed at detecting a physiological burdening of body of a patient by way of acceleration measurement, but merely at determining spiked, abrupt accelerations by individual, jolt-like movements which in the extreme case can result in a one-off deflection of parts of the pump device in the patient body, by which means a suction element with a suction opening could hit a vessel wall or an inner wall of a ventricle, by which means the risk of a suction attachment on this wall is given. A permanent increase of the pump power given an increase physical exertion with above average, but not maximal acceleration values is not ruled out by way of this.

Abrupt, spiked accelerations are hereby to be understood as brief accelerations which could occur for example with standing up procedures. In some embodiments, the brief time can thereby be less than 10 seconds, preferably less than 5 seconds and particularly preferably less than 2 seconds, and thereby within this time frame exceed a threshold with regard to magnitude for example of at least 0.5 $m/s^2$, or for example 1 $m/s^2$. An acceleration rate threshold of more than 1 $m/s^2$, preferably more than 3 $m/s^2$ or 5 $m/s^2$ can be used as an acceleration rate threshold for example. In some embodiment examples, apart from the measured acceleration signals, further variables, such as for example a momentary relative inclination of the pump unit to the gravitational direction are detected, and used for the classification as to whether a relevant spiked or abrupt acceleration was present.

In some embodiments, the acceleration signals are filtered and high-frequency components filtered out for example. Amongst the high-frequency components, hereby for example components of more than 100 Hz, preferably more than 80 Hz, particularly preferably more than 60 Hz are removed by way of a filter, i.e. the cut-off frequency of the filter lies at the mentioned values. A filter can thereby be implemented in a control device as a circuit or as software or firmware.

The invention, apart from the medical field however can also be applied to devices, with which a fluid, for example from a fluid tank, is sucked away by way of a suction conduit or other suction element. This occurs for example in the field of motor vehicles, e.g. in the wiper fluid tank for the windscreen wiper appliance, where wiper water is sucked by an electric pump by way of a hose projecting into the tank. If the vehicle is accelerated on actuating the wiper appliance, the suction hose can move in the tank and hit a wall of the tank. The pump power can be temporarily reduced, in order to avoid a suction attachment there. Accordingly, the invention for example can also be applied to the sucking of fuel from a fuel tank.

A rotation rate (of the pump device or of the suction element) in the context of a radial acceleration or the alignment of a fixed axis direction of the suction element relative to the direction of gravity can also serve as variables derived from the acceleration.

An advantageous design of the invention envisages the pump power being reduced for a limited reaction time period. The reduced pressure in the suction element is directly reduced by way of the reduction of the pump power. The suction pressure in the context of the present application is to be understood as the pressure difference between the fluid pressure in the suction element and the medium surrounding the suction element, wherein the suction pressure is defined in a manner such that it is positive when the absolute hydrostatic pressure in the suction element is lower than the hydrostatic pressure in the environment of the suction element. A reduction of the suction pressure in this context means a reduction of the pressure gradient, i.e. of the pressure difference between the pressure in the suction element and the pressure in the environment of the suction element. The smaller the suction pressure is with regard to this definition, the less rapidly and intensively is the fluid sucked through the suction opening into the suction element.

The invention can moreover be configured in an advantageous manner by way of the speed of a rotation pump being reduced for a limited reaction time period in the case of the use of such a rotation pump. A rotation pump can be activated in a rapid manner with regard to the pump power, and the pump power can be controlled in a stepless manner. The control of the pump power can be effected by way of the control of the electric power of the electric drive motor of the rotor or by way of the control of the power of a micro-turbine which drives the pump, or also by way of setting rotor blades or impellers which are fixedly installed in the casing of the pump.

The reaction time, during which the pump power is reduced, is usually to be understood as a time interval which with regard to its length can be set from the very beginning. Thereby, the reaction time period can be fixed the same for all occurring cases, in which the suction pressure is to be reduced, or it can also be dependent on the conditions which lead to a reduction of the suction pressure, i.e. on the measured acceleration variables. The suction pressure is usually increased again after completion of the reaction time period, which can be effected for example by way of increasing the pump power. If the conditions for a reduction of the suction pressure are fulfilled once again in the meantime, then the reaction time period can also be extended by a further reaction time period. A time interval of less than 20 seconds, less than 10 seconds or less than 5 seconds can be understood as a reaction time for example. The length of the time interval of the reduction of the pump power amongst other things depends on the spiked, abrupt acceleration. Thereby, the pump power is preferably reduced directly after the detection of the spiked, abrupt acceleration, in order to avoid suction effect.

A reduction of the suction pressure can be defined for example by way of a reduction by at least 30% or 50% or 70% or by a reduction of the pump power by at least the corresponding percentages. These magnitudes of reduction can also serve for the definition of the beginning and end of the reaction time period.

A further possibility concerning an advantageous design of the invention envisages a valve in the suction element being at least partly closed at least for a limited reaction time period. The suction pressure can also be temporarily reduced by way of the closure of a valve in the suction element, so that a suction attachment of the suction element can be prevented.

A further advantageous design of the invention envisages the reduction of the suction pressure and/or the reduction of the pump power and/or the closure of the valve in the suction element being effected more rapidly at the beginning of the reaction time period that the increase of the suction pressure and/or the increase of the pump power and/or the opening of the valve, at the end of the reaction time period.

This design is based on the concept of a very rapid reduction of the suction pressure being necessary before the suction element hits the respective wall, given the occurrence of the respective acceleration conditions which give cause to fear a relative movement of the suction element with respect to walls of a cavity, from which fluid is to be sucked. If the condition has normalised after the acceleration, the suction pressure can be increased again by way of a suitable control, without the particular need for a hurry. In contrast, a moderately slow increase of the suction pressure can increase the risk of the suction element being undesirably set into motion due to a jolt which could arise due to an abrupt increase of the suction pressure. The risk of a suction attachment could also be increased by way of such a movement.

A further advantageous design of the invention envisages the maximal spiked acceleration or the jolt in the form of the temporal derivative of the acceleration, or a rotation rate or a relative alignment of the gravitational direction to a fixed axis of the suction element serving as an acceleration variable, which is monitored concerning the exceeding of a threshold. The maximal acceleration which for example is measured directly on the body of a patient or on a device which comprises a cavity, out of which a fluid is to be sucked, can be decisive with regard to the deflection of the suction element in the cavity and thus with regard to the risk of a suction attachment. Elastic restoring forces which after the end of the acceleration effect a restoring of the suction element into an almost neutral position usually act upon the suction element.

A further effect which entails an increased risk of a displacement of the suction element with respect to the walls of the cavity is a sudden change in the acceleration, thus a jolt (jerk). Such a jolt effects particularly large deflections of the suction element given a movement of the body.

According to the invention, the measured acceleration is monitored with regard to exceeding a defined, fixed threshold, or the acceleration is measured and a temporal derivative of the acceleration is continuously evaluated, in order to be able to monitor the jolt with regard to exceeding a certain threshold.

The invention can moreover advantageously be designed such that a temporal integral of the acceleration in a fixed time interval serves as an acceleration variable which is monitored with regard to exceeding a threshold. Thereby, the time interval, over which the acceleration is temporally integrated, can be constantly updated as a rolling time interval. Short acceleration thrusts are taken into consideration to a lesser extent than accelerations which last beyond a certain minimum time period due to this.

The acceleration can be measured by way of an acceleration sensor on a part of the body of the patient, in one or more directions or in a direct manner by way of a sensor on the pump or on an activation unit. The acceleration can be measured in each case in one or more directions.

An acceleration of the patient body can be measured in a particularly simple manner by way of an acceleration sensor being simply fixed externally on the patient. Such an acceleration sensor is advantageously fastened on the abdomen of the patient and not on an extremity.

It is particularly practical if the acceleration sensor or acceleration sensors are able to be fastened directly on the pump or on an activation unit of the pump, so that the acceleration of the pump or of the activation unit can also be monitored in a direct manner. Thereby, in the medical field, one assumes that the pump is integrated into the patient body or fastened on this in a firm which is to say fixed manner, so that the pump directly follows the movements of the body. The suction element in contrast hangs into the cavity in an only partially fixed manner and can move in this in a limited manner given the occurrence of accelerations.

A fixation of corresponding acceleration sensors directly on the pump or an activation unit of the pump entails the advantage that the effort on installation on a body of a patient is reduced, and that the complete pump device, including the acceleration sensors, can be preassembled in a closed manner.

Apart from an operating method of the type described above, the invention also relates to a pump device with at least one pump as well as with a suction element which is connected to this and which has a suction opening, wherein the pump is configured to suck a fluid by way of producing a reduced pressure in the suction element in a cavity, in particular within the body of a patient, wherein the pump device moreover comprises an acceleration measurement device with an acceleration sensor and with a first processing device, as well as a control device which is connected to the first processing device and controls the reduced pressure in the suction element on account of signals of the first processing device, as well as with a second processing device, which in each case for a limited reaction time period reduces the reduced pressure in the suction element in dependence on signals of the first processing device.

The first processing device for example can monitor the measured or continuously determined acceleration variable and detect the exceeding of a threshold. The first processing device for this can for example also continuously integrate acceleration values over time, and monitor the integral over a rolling time period, likewise with regard to exceeding threshold values.

The first processing device then, as soon as the exceeding of a threshold value occurs, can then deliver a signal to the second processing device, said signal influencing the activation of the pump or of a valve and effecting a reduction of the suction pressure for the reaction time period.

Figure 2:
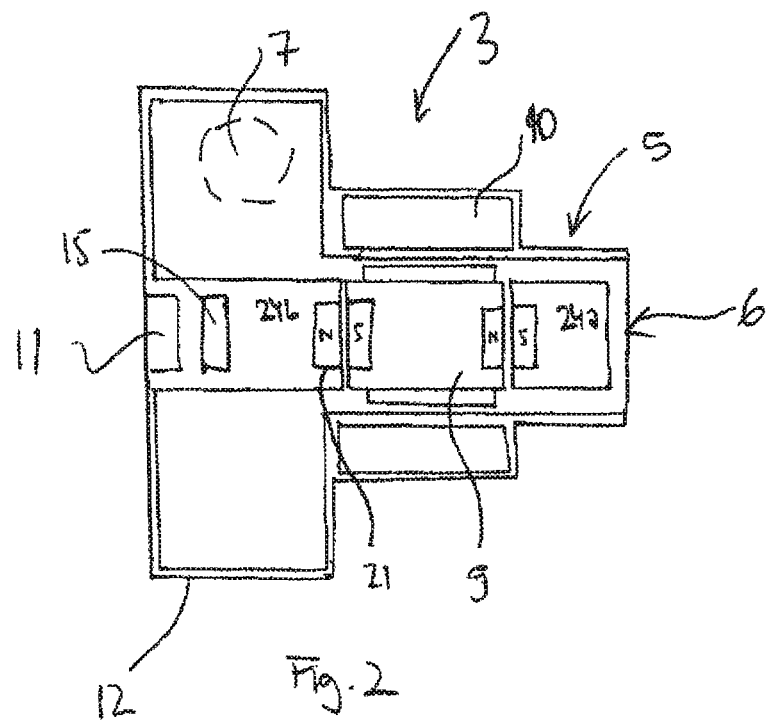

FIG. 1 schematically shows a body of a patient 1 with a ventricle 2, into which a blood pump 3 is introduced. The heart pump is thereby connected to the apex 4 of the ventricle (in this case the left ventricle of the heart, i.e. the pump is a left ventricular assist device or also LVAD). The blood pump 3 is represented in an enlarged manner in FIG. 2.

An inlet piece 5 of the blood pump which is introduced directly into the apex, in the present embodiment example comprises a suction opening 6, through which the blood is sucked in. The blood in the present embodiment example is delivered by way of an axial blood pump with a tangential outlet 7. The outlet 7 is connected to the aorta by way of a cannula 8 or a flexible-tube-like object. The outlet can also alternatively be connected to the pulmonary artery (with a RVAD) or to the shoulder artery. A rotor 9 which is provided with a spiral and which can be set into rotation via a stator 10 of the blood pump, and thus suck blood into the suction opening is located in the inlet piece. An example of such a pump can be deduced from WO2012149946, WO2011054545 or WO2012150045, the disclosure of which is adopted in its entirety into this application by reference.

Further examples of suitable blood pumps are the blood pumps of the EXCOR® or INCOR® series of Berlin Heart GmbH, Berlin, Germany. On using these pumps, the pumps are connected to the hearts via cannulas, so that the suction element can be the inlet of the pump itself as well as the inlet of the cannula connecting the pump to the heart.

The blood pump comprises a control device 11 which for example can be arranged within the pump casing 12 or in an additional housing (of a control unit for example) which is arranged in or outside the body. The control device is connected to at least one acceleration sensor (in a wireless manner or by wire). The acceleration sensor is configured in a manner such that this measures an acceleration in one or more directions. In the represented example, three acceleration sensors are represented, although also one acceleration sensor can be sufficient.

The acceleration sensor 13 is arranged in an external control unit which is carried directly on the body. The acceleration sensor 14 is arranged on the body or subcutaneously and communicates with the control device via a wireless connection. The acceleration sensor 15 is arranged within the pump casing, and thereby in one variant can be arranged within the part of the blood pump, through part which blood flows, or in further variant can be arranged in a part of the blood pump which does not come into contact with the delivered blood, i.e. in this variant the acceleration sensor can be arranged for example within the stator housing or on the outer region of the housing. The different locations, at which an acceleration sensor can be arranged in each case have different advantages and disadvantages compared to one another. The inlet piece 5 as a suction element is represented at the distal end of the blood pump. In some embodiments, the suction opening can be covered with a fluid permeable grating.

Figure 3:
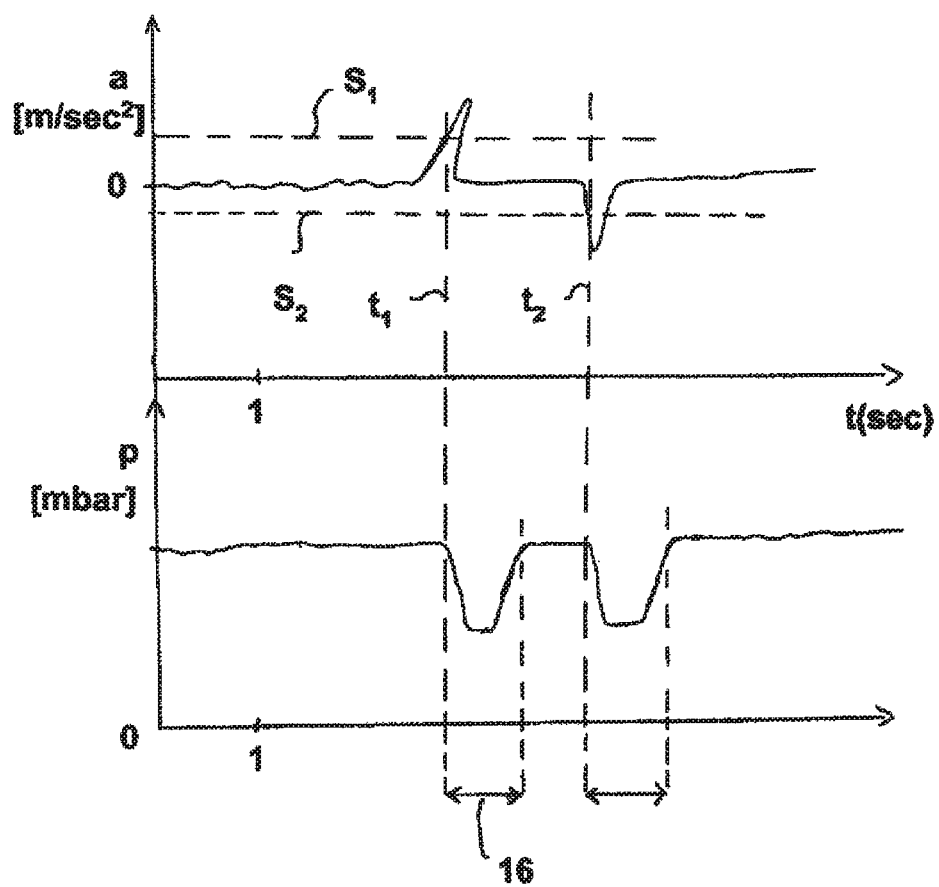

FIG. 3 shows a diagram with which the time in seconds is plotted on the x-axis, whereas acceleration is represented in the upper part of the diagram on the y-axis. Two vertical dashed lines $t_1$, $t_2$ are represented, of which the point in time $t_1$ corresponds to the first point in time, at which the monitored acceleration exceeds a threshold value $s_1$. It is clear from the lower part of the diagram that the suction pressure which is plotted on the y-axis and is indicated at p is constant up to the point in time $t_1$. The activation device of the pump device has the effect that the suction pressure is immediately reduced on exceeding the threshold $s_1$. This manifests itself in the lower part of FIG. 3, where the suction pressure drops after the point in time $t_1$ and only after the passing of the reaction time period 16 has its again approximately reached the previously high level gain, for example by at least 70%. Hardly any fluid is sucked through the suction opening during the reaction time period 16, so that a suction attachment of the suction element on a vessel wall is unlikely.

The reaction time period can either be defined as a time period, during which the suction pressure is reduced by a minimum percentage or a defined absolute value, or as a time period which begins with the exceeding of a threshold concerning the monitored acceleration variable (at the point in time $t_1$) and is completed with the renewed increase of the suction pressure to a defined minimum percentage, e.g. 70% of the suction pressure before the beginning of the reaction time period.

As a result, an exceeding of the second threshold $s_2$ occurs at the point in time $t_2$, at which an acceleration in a direction opposite to the first acceleration is measured. It is useful to only monitor the magnitude of the acceleration, so that an activation of the pressure reduction occurs independently of the direction of the acceleration. One can also recognise in the lower part of FIG. 3 that the suction pressure in the suction element is lowered for a reaction time period after the point in time $t_2$, at which a the exceeding of a threshold value of the acceleration variable takes place. The above description is referred to concerning exemplary variables and time.

Figure 4:
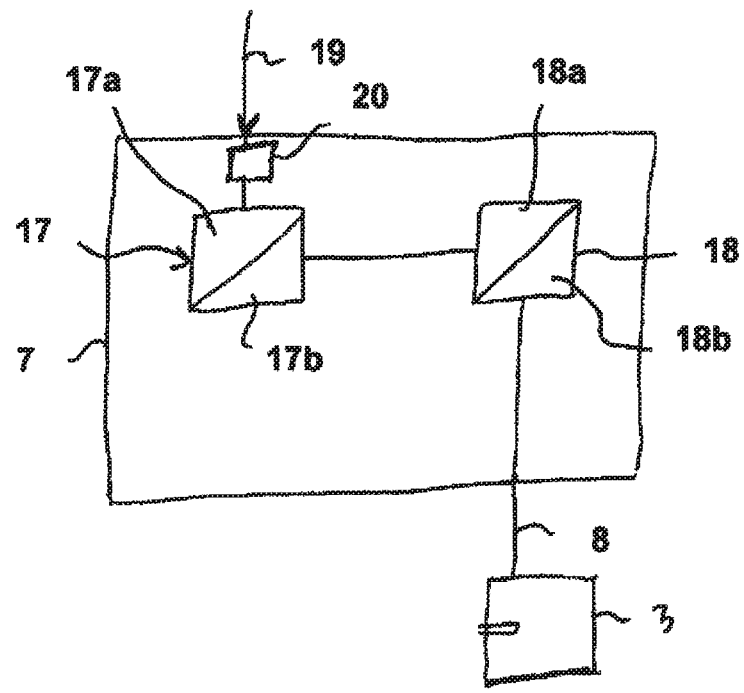

FIG. 4 shows a control device 11a with a first processing device 17 and with a second processing device 18. A sensor lead 19 is represented, which connects the control device 11a to an acceleration sensor which is not represented in FIG. 4, or to a gyroscope. The sensor lead at the input of the control device 17 is connected to a digital/analog converter 20 or directly by way of suitable data buses (I2C-buses or SPI-buses), to the control device which leads corresponding acceleration signals in digitalised form to the first processing device 17. There, in an input region 17a, the acceleration values are continuously monitored and, as the case may be, more complex acceleration variables, such as an acceleration integral over a fixed time or the jolt are continuously computed. The continuous comparison with a defined threshold takes pace in a comparison module 17b, and a signal production takes pace as the case may be, given the exceeding of the threshold. A corresponding signal is led to the second processing device 18. The second processing device 18 examines as to whether the pressure has already dropped, since an adequate acceleration was detected already shortly before this, and as to whether the reaction time was extended on account of this. If an exceeding of an acceleration threshold occurs for the first time, then the motor comprising the rotor 9 and the stator 10 is activated by the second processing device 18, in a manner such that the pump power is temporarily reduced for the reaction time period. The feed current or the voltage of the motor is accordingly reduced, so that the speed of the rotor reduces. The second processing device 18 for this comprises a time base 18a and a signal output 18b.

Figure 5:
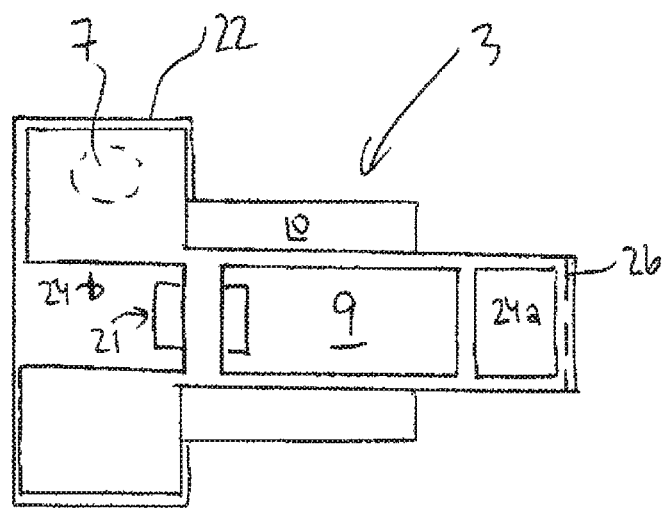

FIG. 5 in an enlarged form shows a more detailed representation of a rotation pump with a pump casing 22, which is an axial pump. The pump casing accommodates a rotor 23 which is mounted in an active, axially magnetic manner between a hub and a casing wall or two hubs 24a, 24b, and is controlled for example by way of at least one control coil. The rotor is moreover passively radially mounted via magnets 21 which are arranged in the hubs or in the casing. The rotor can alternatively also be hydrodynamically mounted or be mounted by a combination of hydrodynamic and magnetic bearings. Either the speed of the rotor 23 is lowered for reducing the suction pressure in the suction element, or the rotor can be deformed by way of a magnetic field such that its pump power reduces given a constant rotation.

However, one can moreover also provide a valve which is represented schematically by a dashed line 26. This valve for example can have the form of an iris diaphragm or flap valve and be externally controllable in each case. The valve can be arranged in the pump casing 22 as well as in the suction element or in the region of an outlet element of the blood pump. A reduction of the suction pressure in the suction element for a reaction time period can also be achieved by way of closure or partial closure of the respective valve.

A simple and reliable means is created, in order to prevent the suction attachment of a suction element of a pump on the walls of a cavity, out of which a fluid is to be delivered, by way of the invention.

LIST OF REFERENCE NUMERALS 1 patient body
2 heart chamber
3 blood pump
4 apex
5 inlet piece
6 suction opening
7 outlet
8 cannula
9 rotor
10 stator
11, 11a control device
12 pump casing
13 first acceleration sensor
14 second acceleration senor
15 third acceleration senor
16 reaction time period
17 first processing device 17a input part
17b comparison module
18 second processing device
18a time base
18b signal output
19 sensor lead
20 digital/analog converter
21 permanent magnets
22 pump casing
23 rotor
24a,b hub
25 delivery element
26 valve
$t_1, t_2$ points in time
$s_1, s_2$ acceleration thresholds

The invention claimed is:

1. A method for the operation of a pump device, the pump device comprising a pump and a suction element, said suction element being connected to the pump and having a suction opening, the method comprising:
    sucking a fluid with the pump thereby producing a reduced pressure in the suction element, in a cavity;
    measuring and monitoring an acceleration during the operation of the pump device; and
    reducing the reduced pressure in the suction element at least for a limited reaction time period based on an occurrence of a spiked, abrupt acceleration variable or a variable derived from the spiked, abrupt acceleration variable, which lies above a fixed threshold value.

2. The method of claim 1 further comprising reducing a pump power of the pump for a limited reaction time period.

3. The method of claim 2, wherein the pump is a rotation pump, the method further comprising reducing a speed of the rotation pump for the limited reaction time period.

4. The method of claim 1 further comprising closing, at least partly, a valve in the suction element at least for a limited reaction time period.

5. The method of claim 1 further comprising reducing at least one of a suction pressure of the suction element, a pump power of the pump, or a closure of a valve in the suction element more rapidly at the beginning of the reaction time period than an increase of at least one of a suction pressure of the suction element, a pump power of the pump, or an opening of a valve of the suction element towards the end of the reaction time period.

6. The method of claim 1 further comprising a maximum of a spiked acceleration or a jolt in the form of a temporal derivative of the acceleration, or a rotation rate serve as acceleration variables which are monitored with regard to exceeding a threshold.

7. The method of claim 1, wherein a temporal integral of the acceleration in a fixed time interval serves as the monitored acceleration variable, which is monitored with regard to exceeding a threshold.

8. The method of claim 1, wherein the cavity is in a patient body, and an acceleration of a part of the patient body is measured in one or more directions.

9. The method of claim 1, wherein the cavity is in a patient body, and an acceleration of the pump or an activation unit of the pump in or on the patient body is measured in one or more directions.

10. The method of claim 1, wherein the cavity is in a body of a patient.

11. A pump device comprising:
    a pump; and
    a suction element which is connected to the pump and has a suction opening, wherein the pump is configured to suck a fluid by production of a reduced pressure in the suction element that is in a cavity and
    an acceleration measurement device comprising an acceleration sensor, a first processing device, a second processing device, and a control device which is connected to the first processing device and is configured to control the reduced pressure in the suction element based on a first set of signals of the first processing device, wherein the second processing device is configured to reduce the reduced pressure in the suction element in each case for a limited reaction time period, based on a second set of signals of the first processing device.

12. The pump device of claim 11, wherein the cavity is in a body of a patient.

* * * * *